United States Patent [19]
Savage et al.

[11] Patent Number: 6,103,768
[45] Date of Patent: Aug. 15, 2000

[54] FATTY ACID BASED COMPOSITIONS AND METHODS FOR THE CONTROL OF PLANT INFECTIONS AND PESTS

[75] Inventors: Steven D. Savage, San Marcos; Steven L. Evans; Robert A. Haygood, both of San Diego; Paul S. Zorner, Carlsbad; Keith Jones, San Diego, all of Calif.

[73] Assignee: Mycogen Corporation, San Diego, Calif.

[21] Appl. No.: 08/925,561

[22] Filed: Sep. 8, 1997

Related U.S. Application Data

[60] Division of application No. 08/400,724, Mar. 8, 1995, abandoned, which is a continuation-in-part of application No. 08/237,080, May 3, 1994, which is a division of application No. 07/871,511, Apr. 23, 1992, Pat. No. 5,366,995, which is a continuation-in-part of application No. 07/694,193, May 1, 1991, abandoned.

[51] Int. Cl.$^7$ .......... A01N 37/18; A01N 29/00; A01N 43/00; A01N 43/36; A01N 43/40; A01N 43/48; A01N 43/50; A01N 43/52; A01N 43/653; A01N 59/14; A01N 59/16; A01N 59/22

[52] U.S. Cl. .............. 514/627; 514/24; 514/25; 514/27; 514/33; 514/35; 514/37; 514/42; 514/63; 514/250; 514/255; 514/274; 514/365; 514/376; 514/383; 514/391; 514/394; 514/395; 514/399; 514/417; 514/433; 514/476; 514/479; 514/483; 514/491; 514/492; 514/494; 514/499; 514/500; 514/525; 514/528; 514/538; 514/620; 514/625; 514/629; 514/634; 514/646; 514/667; 514/668; 514/669; 514/670; 514/671; 514/672; 514/681; 514/682; 514/728; 514/731; 514/736; 514/737; 514/764; 424/623; 424/630; 424/631; 424/632; 424/633; 424/634; 424/635; 424/637; 424/638; 424/641; 424/658; 424/661; 424/665; 424/703; 424/705; 424/713; 424/714; 424/93.1

[58] Field of Search .................... 514/625, 627, 514/629, 24–25, 27, 33, 35, 37, 42, 63, 250, 255, 274, 365, 376, 383, 391, 394, 395, 399, 417, 433, 475, 476, 479, 483, 491, 492, 494, 499, 500, 525, 528, 538, 620, 624, 634, 646, 667–672, 681, 682, 728, 731, 736, 737, 764; 424/93.1, 623, 630–635, 637, 638, 641, 658, 661, 665, 703, 705, 713, 714; 504/117

[56] References Cited

U.S. PATENT DOCUMENTS

| | | | |
|---|---|---|---|
| 3,193,451 | 7/1965 | Reinisch | 514/627 |
| 3,285,809 | 11/1966 | Mod et al. | 514/625 |
| 3,285,812 | 11/1966 | Mod et al. | 514/237.5 |
| 3,931,412 | 1/1976 | Kensler et al. | 424/311 |
| 3,931,413 | 1/1976 | Frick et al. | 424/311 |
| 3,954,977 | 5/1976 | Rife | 514/66 |
| 3,983,214 | 9/1976 | Misato et al. | 514/53 |
| 4,002,775 | 1/1977 | Kabara | 426/532 |
| 4,263,321 | 4/1981 | Lover et al. | 514/625 |
| 4,707,496 | 11/1987 | Simmons | 514/531 |
| 4,771,571 | 9/1988 | Obrero et al. | 47/58.1 |
| 4,774,234 | 9/1988 | Puritch et al. | 514/86 |
| 4,826,678 | 5/1989 | Gaudet et al. | 424/93.461 |
| 4,861,762 | 8/1989 | Puritch et al. | 514/122 |
| 4,870,102 | 9/1989 | Puritch et al. | 514/493 |
| 4,891,385 | 1/1990 | Synek | 514/490 |
| 4,904,645 | 2/1990 | Puritch et al. | 514/65 |
| 5,093,124 | 3/1992 | Kulenkampff | 424/406 |
| 5,192,546 | 3/1993 | Abercrombie | 424/405 |
| 5,246,716 | 9/1993 | Sedun et al. | 424/713 |
| 5,496,857 | 3/1996 | Targosz | 514/617 |
| 5,614,558 | 3/1997 | James et al. | 514/574 |
| 5,681,859 | 10/1997 | James et al. | 514/625 |
| 5,906,961 | 5/1999 | Roberts et al. | 504/116 |
| 5,998,475 | 12/1999 | James et al. | 514/556 |

FOREIGN PATENT DOCUMENTS

| | | |
|---|---|---|
| B 135211 | 4/1978 | Australia . |
| 2596617 | 10/1987 | France . |
| 1567187 | 6/1970 | Germany . |
| 0214134 | 11/1980 | Germany . |
| 3342529 | 11/1983 | Germany . |
| 3309765 | 9/1984 | Germany . |
| 56-043207 | 4/1981 | Japan . |
| 257642 | 4/1949 | Sweden . |
| 907842 | 10/1962 | United Kingdom . |
| 1219077 | 1/1971 | United Kingdom . |
| 1438946 | 6/1976 | United Kingdom . |

OTHER PUBLICATIONS

Ahmed, S.M. et al., (1985) "Preparation and Characterization of Derivatives of Isoricinoleic Acid and Their Antimicrobial Activity" JAOCS 62(11):1578–1580.

Chase A.R. (1983) "Influence of an Insecticidal Soap on Several foliar Diseases of Foliage Plants" Plant Disease 67(9):1021–1023.

Puritch, G.S. et al., (1981) "Effect of Fatty Acid Salts on the Growth of *Botrytis cinerea*" Canadian Journal of Botany 59(4):491–494.

Kabara, J.J. (1987) "Fatty Acids and Esters as Antimicrobial/Insecticidal Agents" Ecology and Metabolism of Plant Lipids, Chapter 14, pp. 220–238.

Kabara, J.J. et al., (1972) "Fatty Acids and Derivatives as Antimicrobial Agents" 2(1):23–28.

Kabara, J.J. (1984) "Antimicrobial Agents Derived from Fatty Acids" JAOCS 61(2):397–403.

Kabara, J.J., et al., (1977) "Antimicrobial Lipids: Natural and Synthetic Fatty Acids and Monoglycerides" Lipids 12(9):753–759.

Frick, E.L., R.T. Burchill (1972) "Eradication of Apple Powdery Mildew From Infected Buds" Plant Disease Reporter 56(9):770–772.

Novak, A.F., et al. (1969) "Antimicrobial Activity of Some N–Substituted Amides of Long–Chain Fatty Acids" Chemical Abstracts 72(9):124, abstract no. 40091y.

Journal of the American College of Toxicology, vol. 5, No. 5, 1986, pp. 417–429.

*Primary Examiner*—John Pak
*Attorney, Agent, or Firm*—Saliwanchik, Lloyd & Saliwanchik

[57] ABSTRACT

The invention described here concerns the unique utility of fatty acids and their derivatives to eradicate existing fungal and bacterial infections in plants. Also, described herein are combination treatments whereby fatty acids are used to enhance or augment the activity of fungicides, bactericides, and biological control agents.

13 Claims, No Drawings

FATTY ACID BASED COMPOSITIONS AND METHODS FOR THE CONTROL OF PLANT INFECTIONS AND PESTS

CROSS-REFERENCE TO A RELATED APPLICATION

This is a division of application Ser. No. 08/400,724, filed Mar. 8, 1995 now abandoned; which is a continuation-in-part of application Ser. No. 08/237,080, filed May 3, 1994; which is a division of Ser. No. 07/871,511, filed Apr. 23, 1992, now U.S. Pat. No. 5,366,995; which is a continuation-in-part of Ser. No. 07/694,193, filed May 1, 1991, now abandoned.

FIELD OF THE INVENTION

This invention pertains generally to the fields of insect pest control and the control of bacterial and fungal plant infections. Fatty acid compositions are provided for each of these applications.

BACKGROUND OF THE INVENTION

A. Control of fungal and bacterial plant infections. The protection of desirable plants and their produce from fungal and bacterial pathogen infection has traditionally required preventative applications of fungicidal or bactericidal agents. Fungicidal and bactericidal compounds have long been used to increase yields and extend agricultural production capabilities into new areas. They have also been extremely important tools for ameliorating season-to-season differences in yield and quality caused by weather-driven variations in disease pressure.

The future role of fungicides and bactericides in agriculture is increasingly threatened by several factors including; the development of pest resistance, increasing concerns about food safety, and environmental accumulation of toxic compounds. As older fungicides and bactericides are removed from the market due to regulatory changes, and new fungicides and bactericides are becoming increasingly expensive to register, there is an increasing need to find ways to more wisely use the remaining, safest fungicides. This is particularly true for the many crop/disease combinations which do not represent large enough markets to pay for the cost of new compound registration. Wiser fungicide and bactericide use will include ways to reduce application rates (and thus potential residues), finding ways to extend registrations to new crops, and identifying new fungicidal and bactericidal compositions and treatments to combat the development of pest resistance.

Chemical fungicides and bactericides have provided an effective method of control; however, the public has become concerned about the amount of residual chemicals which might be found in food, ground water and the environment. Stringent new restrictions on the use of chemicals and the elimination of some effective pesticides from the market place could limit economical and effective options for controlling fungi and bacteria.

It is well recognized by those skilled in this art that there is a clear distinction between preventative microbicidal (fungicidal and bactericidal) activity and curative activity. Compositions and methods which may be effective to prevent microbial growth may have very little or no impact on established infections. Of course, it is often desirable to prevent infections altogether, however, this is not always possible and there is a great need for compositions which have the unique ability to arrest the growth of established infections. This is particularly true in the control of infections which become established on agricultural products after harvest.

Curative fungicidal activity has been observed when some biological agents are used for disease control (e.g., strain of Bacillus subtilis) and this activity can usually be attributed to the production of antibiotic compounds by the biocontrol organism. Because expensive toxicological screening and residue/metabolite monitoring may be required for such an antibiotic, the normal registration-costadvantage of these non-chemical agents is diminished. Biological control agents which do not make antibiotics would be much easier to register, but they tend to have only preventive control.

The commercialization of disease biocontrol agents has also been hampered by inconsistent field performance. Organisms which show biocontrol potential in laboratory and greenhouse experiments often fail to compete with the existing microflora when applied outdoors and are thus unable to express their biocontrol potential, regardless of mode of action. Specifically there is a need for disease control methods which are more compatible with the need for affordable and effective disease control, a high degree of food safety, and minimal environmental impact.

One example of the need to control post-harvest spoilage of agriculture products pertains to green and blue molds of citrus fruits caused by *Penicillium digitatum* and *P. italicum*. These molds cause severe damage during storage and shipping. The existing fresh-market industry relies completely on a combination of several chemical treatments to deliver sound fruit to distant markets over substantial periods of time without excessive damage caused by these molds. Unfortunately, there are increasing concerns about the safety of the chemicals currently used to control these fungal pathogens. Also, there are increasing problems with fungal strains with resistance to the most effective compounds.

In another example, powdery mildew of grapes caused by *Uncinula necator* can cause severe damage even in dry areas such as California. Traditionally this disease was controlled with applications of elemental sulfur, but this necessitates frequent, high volume applications of an irritating material. The introduction of egosterol biosynthesis inhibiting fungicides (primarily triazoles) greatly simplifies control, but also selects for tolerant strains. Some of these compounds are also known to have potential teratogenic effects and very long soil residuals. In these and other examples, alternative control methods are in great demand—particularly methods which are safer or more environmentally benign.

Fatty acids are a class of natural compounds which occur abundantly in nature and which have interesting and valuable biological activities. The in vitro activity of fatty acids against many medically important fungi and bacteria is well known; however, their in vivo antifungal activity is often very limited and it is difficult to predict on the basis of in vitro experiments. There is a much smaller body of literature concerning the activity of fatty acids and their derivatives against pathogens on agricultural crops. Ahmed et al. (Ahmed, S. M., F. Ahmad, S. M. Osman [1985] *JAOCS* 62:1578–1580) report in vitro inhibition of radial growth of several fungal genera with plant pathogenic representatives. Recently there has been an expanding use of "insecticidal soaps" in agriculture which are salts of certain fatty acids. This has resulted in a few observations of impact on fungal disease. For instance, Chase et al. (Chase, A. R., L. S. Osborne [1983] *Plant Disease* 67:1021–1023) observed that applications of an 18:1 fatty acid salt "insecticidal soap" gave moderate preventive control of two foliage plant diseases and actually exacerbated two other diseases. Puritch et al. described the effect of fatty acid salts on fungi in vitro (Puritch, G. S., W. C. Tan, J. C. Hopkins [1981] *Canadian Journal of Botany* 59(4):491–494). Nickel and silver salts of fatty acids have been used to control pathogens on plants. GB Patent Nos. 907,842 and 1,219,077. In U.S. Pat. No. 3,983,214, Misato et al. claim a fungicidal composition containing a sucrose fatty acid ester. Misato et al. emphasize the preventative activity of their composition. Similarly, in U.S. Pat. No. 4,771,571, Obrero et al. describe a method of preventing infections of pineapple by treating the fruit, while on the bush, with a surfactant. In U.S. Pat. No. 4,002,775, Kabara et al. claim microbicidal food additives comprising 1 or 2-mono-laurin polyol ester. Kabara's work is also described in: Chapter 14 of *Ecology and Metabolism of Plant Lipids,* American Chemical Society (1987); "Fatty Acids and Derivatives as Antimicrobial Agents," In: *Antimicrobial Agents and Chemotherapy,* American Society for Microbiology (1972), pp. 23–28; "Antimicrobial Agents Derived from Fatty Acids," (1984) *JAOCS* 61(2):397–403; and "Antimicrobial Lipids: Natural and Synthetic Fatty Acids and Monoglycerides," *Lipids* 12(9):753–759. Also, the use of fatty acid esters and alcohols for the control of powdery mildew on apple buds has been described (Frick, E. L., R. T. Burchill [1972] *Plant Disease Reporter* 56:770–772; U.S. Pat. No. 3,931,413). In the '413 patent, Frick et al. emphasize the phytotoxicity of fatty acids and state that the acid or salt form should only be used on dormant plant tissue. The phytotoxicity of fatty acids and their salts is well documented and has long been believed to be a barrier to the use of these compositions on living plants. See U.S. Pat. No. 5,246,716.

Most in vitro tests for antimicrobial activity involve monitoring the germination and growth of pathogen propagules in a liquid or solid format in which there is exposure to the chemical agent. These assays are directly analogous to preventive applications in an agricultural setting—applications which are made prior to the time when the pathogen initiates an infection. The primary screening process for synthetic chemicals in industrial settings is almost exclusively based on in vitro and preventive in vivo testing. Thus, compounds without significant preventive activity are rejected. There are no reports of fatty acids acting in a curative mode (applied after fungal infection is established).

B. Pest control. Insects and other pests cost farmers billions of dollars annually in crop losses and in the expense of keeping these pests under control. The losses caused by pests in agricultural production environments include decrease in crop yield, reduced crop quality, and increased harvesting costs.

Chemical pesticides have provided an effective method of pest control; however, the public has become concerned about the amount of residual chemicals that might be found in food, ground water, and the environment. Stringent new restrictions on the use of pesticides and the elimination of some effective pesticides from the market place could limit economical and effective options for controlling costly pests. Thus, there is an urgent need to identify pest control methods and compositions which are not harmful to the environment. Various pesticidal compositions having a fatty acid component, or a fatty acid derivative as a component, are well known to those skilled in the art. See, for example, U.S. Pat. No. 5,192,546; DE Patent 3,342,529; Australian Patent No. AU-B 1-35-221/78; and U.S. Pat. Nos. 4,774, 234; 4,826,678; 4,904,645; 4,870,102; 4,861,762; 4,707, 496; 3,954,977; 5,093,124; and 4,891,385. None of these patents described pesticide activity for amide derivatives of fatty acids.

BRIEF SUMMARY OF THE INVENTION

The subject invention concerns materials and methods for the control of fungal and bacterial plant pathogens and for the control of pests such as insect pests. The materials and methods of the subject invention utilize fatty acid compositions which are both highly effective and non-hazardous to the environment. As described more fully herein, the invention can be thought of in terms of three primary embodiments.

In a first embodiment, the subject invention pertains to the discovery that fatty acids, their salts and derivatives, when used at the appropriate concentration range and timing, are useful for the eradication of established fungal and bacterial infections in or on plant tissues. Thus, the subject invention provides parameters of application which allow the useful application of these agents for the control of plant disease. In a specific example of this embodiment of the subject invention, the fatty acid component is applied to non-dormant plant tissue.

According to this first embodiment of the subject invention, established fungal and bacterial infections are effectively controlled by compositions comprising one or more substituted (or unsubstituted) saturated (or unsaturated) fatty acids (or their salts or derivatives). The fatty acids of the subject invention can be from about C7 to about C20 and can be, for example, in the epoxide, lactone, cyclopropane, methylated, or hydroxylated forms.

Specifically exemplified herein are saturated and mono-unsaturated fatty acids of length C9, C12, and C18. The use of the compositions described here, when used in the proportions and application rates set forth more fully hereinafter, results in an unexpected control of established fungal infections. The lack of preventive activity of these compositions makes this discovery highly unexpected. This invention demonstrates that the same fatty acids which lack preventive activity for disease control exhibit advantageous curative control. This activity is most advantageous over a range of concentrations between low doses which are ineffective and higher doses which are phytotoxic to the host plant. This critical range varies with the form of the acid (free acid, salt, formulation) and the host/pathogen system under consideration, but can be determined by a person skilled in this art using the teachings of the subject invention.

The discovery of curative activity for fatty acids has further significance because that utility along with the non-phytotoxic properties of these compounds make them extremely useful for combinations with other disease control agents. Thus, fatty acids can be advantageously combined with other disease control chemicals. In one example, fatty acids can be combined with preventative antifungal or antibacterial agents. Specifically exemplified herein is the use of fatty acid compounds in conjunction with formulations containing elemental sulfur which are widely used for preventative antifungal treatment.

A second major embodiment of the subject invention pertains to combination treatments whereby fatty acids (or their salts or derivatives) are combined with biological control agents. An important limitation of live biological control agents is their inability to compete with resident microflora. This problem can be overcome in accordance with the teachings of the subject invention. The application of a fatty acid composition to a plant surface in accordance with the teachings of the subject invention can be used to substantially disrupt the existing balance of microorganisms. This provides an opportunity for appropriately selected, live biological control agents to become established on the plant surface. When these "disrupted microbial niches" are re-colonized a microorganism which is particularly adapted to surviving that disruption event is more reliably established during subsequent colonization episodes.

In the case of bacterial disease episodes, many of which involve an epiphytic build-up phase, the fatty acid can be used to reduce the pathogen population and simultaneously open the way for subsequent colonization by desirable microorganisms. Colonization by desirable microbes can be even further enhanced by applying a fatty acid, an enrichment agent (e.g., a particular nutrient source such as starch, cellulose or other macromolecular foodbase) and an organism particularly suited to survival and growth in that specific regime of negative and positive selection agents. Also, the fatty acid itself or its breakdown products can provide the foodbase which favors colonization by a certain organism. Alternatively, the food base can consist of the addition of another agent in the formulation.

Thus, a second major embodiment of the subject invention is the use of fatty acids, their salts, or derivatives, as "niche-clearing" agents.

In the third major embodiment of the subject invention, certain amide derivatives of fatty acids have been discovered which have excellent pesticidal activity. Specifically exemplified are fatty acid compositions, such as cocoate, which has been reacted with diethanolamine to produce cocoamide DEA. As is known in the art, cocoate is a mixture of free fatty acids derived from a "cracking" of coconut oil. The mixture consists primarily of C12 and C14 saturated fatty acids.

The fatty acids of the subject invention and their derivatives are highly advantageous for pesticidal use because they occur commonly in nature, have little mammalian toxicity, are compatible with other biological control strategies and are readily broken down to innocuous components.

Thus, among the advantages and the embodiments of the subject invention are the following:

- the use of a fatty acid as the active ingredient in a composition to eradicate existing phytopathogens such as fungal infections or bacterial colonization;
- the use of a fatty acid to improve or compliment the activity of other fungicidal and bactericidal chemicals;
- the combination of curative fatty acids with preventive biological control agents to provide an enhanced scope of protection;
- the use of a curative fatty acid to provide control and to also perturb the plant surface microflora to enhance the subsequent colonization of that surface by a compatible biological control agent;
- the combined use of a fatty acid, an enrichment agent and a biological control agent which is tolerant to the fatty acid and favored by the enrichment agent; and
- the combined use of a fatty acid with or without an enrichment agent to disrupt microbial colonization and enhance subsequent colonization by a biocontrol agent;
- the combined use of a fatty acid and a prophylactic antimicrobial to provide both curative and preventive control of microbial plant infections;
- the use of nitrogen-containing fatty acid derivatives, both for control of microbial infections and for pesticidal use.

DETAILED DESCRIPTION OF THE INVENTION

The subject invention concerns unique materials and methods for the effective and environmentally safe control of insect pests and microbial plant pathogens. In each embodiment of the subject invention, fatty acid compositions constitute a critical component of the control strategy. As described in detail below, the fatty acid component may be in the acid form or may be a salt or derivative. As used herein, reference to "fatty acid" should be understood to include salts and derivatives thereof as described herein unless the context clearly pertains only to the acid form. For certain applications, the use of a particular fatty acid derivative is a critical aspect of the invention. For example, diethanolamine amides of C12 fatty acids have been discovered to have particular surprising activity against insects. For the control of fungi and bacteria, it is possible to use a variety of fatty acids and their salts and derivatives. However, even for antifungal and antibacterial applications, certain fatty acids, their salts, or their derivatives are preferred as described herein.

The common theme to the invention described herein is the use of environmentally friendly fatty acid compositions in methods to control pests or microbes. The invention can best be understood by reference to three primary embodiments. First, the subject invention pertains to direct curative control of fungal or bacterial plant pathogens with fatty acid compositions. In this embodiment, the activity of the fatty acid compositions can be enhanced or supplemented by using the fatty acid component in conjunction with chemical or biological agents to achieve the desired control. In one specific embodiment, a fatty acid derivative is used in conjunction with a sulfur compound to achieve excellent antimicrobial activity without phytotoxicity.

In a second major embodiment of the subject invention, fatty acid compositions are used to clear away existing microorganisms on a plant or in another natural setting, and desired microbes are then introduced with a greatly enhanced opportunity to colonize the site. The desired microbes may be, for example, insecticidal, or they may express insecticidal proteins. This embodiment of the invention is referred to herein as "niche-clearing."

In a third major embodiment, specific fatty acid derivatives have been discovered which have highly advantageous pesticidal activity. Specifically exemplified are nitrogen-containing amide derivatives of C12 fatty acids.

Each of these three major embodiments is discussed in detail below. Before detailing the three major embodiments, a general description of the fatty acid compositions useful according to the subject invention is provided.

I. Fatty Acid Compositions

Fatty acid compositions useful according to the subject invention can be unsubstituted, or substituted, saturated, or unsaturated, fatty acids (or their salts or derivatives), of about C7 to about C20. Specifically exemplified are fatty acids of length C9, C12, C14, and C18 typified by, but not limited to, pelargonic acid, lauric acid, myristic acid, oleic acid, and various salts, amides, or esters of these acids. The fatty acid component of the subject invention may be a single fatty acid or salt, or a mixture of two or more fatty acids or salts thereof. The fatty acid salts which can be used according to the subject invention include, but are not limited to, sodium, potassium, and nitrogen-containing salts including isopropylamine salts. Also, various esters and amides are useful according to the subject invention, including monoethylene glycol ester and DEA amides. The fatty acid amide derivatives described herein have been discovered to have both antimicrobial and pesticidal activity.

The fatty acid compounds useful according to the subject application can be represented by the following formula:

in the case of curative control of established microbial infections,

Z=O, N, or S $R_1$=C5 to C19 saturated or unsaturated hydrocarbon, or an epoxide, or cyclopropane thereof $Y_1$=H, $C_1$–$C_5$ hydrocarbon, or hydroxyl at any position along $R_1$ $Y_2$=H, $C_1$–$C_5$ hydrocarbon, or hydroxyl at any position along $R_1$ $R_2$=$C_1$–$C_{10}$ saturated or unsaturated, branched or unbranched, hydrocarbon having at least one hydroxyl group at any position on $R_2$; salt; or H.

The fatty acid compounds claimed according to the subject invention for use in combination with live biocontrol agents, as "niche-clearing" agents, or as a pesticide, can also be represented by Formula I wherein:

Z=O, N, or S $R_1$=C5 to C19 saturated or unsaturated hydrocarbon, or an epoxide, or cyclopropane thereof $Y_1$=H, $C_1$–$C_5$ hydrocarbon, or hydroxyl at any position along $R_1$ $Y_2$=H, $C_1$–$C_5$ hydrocarbon, or hydroxyl at any position along $R_1$ $R_2$=$C_1$–$C_{10}$ saturated or unsaturated, branched or unbranched, hydrocarbon which may have one or more hydroxyl groups at any position on $R_2$; carbohydrate; salt; or H.

In a preferred embodiment of the invention, $R_2$ is selected from the group consisting of aliphatic amines which form cationic aliphatic amonium compounds; $K^+$; $Na^+$; and $H^+$. Oleic, linoleic, linolenic, lauric, capric, myristic, palmitic, and pelargonic acids and their salts and esters are particularly useful according to the subject invention. We have also found that the monoethylene glycol ester of fatty acids is particularly useful according to the subject invention.

As those skilled in the art would readily recognize, when Z=N, there will be two R groups attached to N. Thus, in this specific case of Formula I, the formula can be represented as follows:

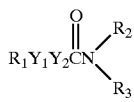

wherein $R_1$=C5 to C19 saturated or unsaturated hydrocarbon, or an epoxide, or cyclopropane thereof $Y_1$=H, $C_1$–$C_5$ hydrocarbon, or hydroxyl at any position along $R_1$ $Y_2$=H, $C_1$–$C_5$ hydrocarbon, or hydroxyl at any position along $R_1$ $R_2$=$C_1$–$C_{10}$ saturated or unsaturated, branched or unbranched, hydrocarbon which may have one or more hydroxyl groups at any position on $R_2$; carbohydrate; salt; or H;

$R_3$=$C_1$–$C_{10}$ saturated or unsaturated, branched or unbranched, hydrocarbon which may have one or more hydroxyl groups at any position on $R_2$; carbohydrate; salt; or H.

As described more fully herein, compounds of Formula IA are useful both as fungicides and pesticides. Of particular interest are certain diethanolamine (DEA) fatty acid compounds. It is well known in the art that DEA fatty acid compounds can be prepared by reacting fatty acids with diethanolamine. These compounds can be readily prepared from fatty acid compositions including fatty acid-containing natural products derived from coconut oil. Specific examples of such products include, but are not limited to, cocoamide DEA, non-ionic coconut amides, coconut diethanolamides, and fatty diethanolamides. These products are available under a variety of commercial names including the "AMIDEX" series, Chemron Corp.; "INCROMIDE CA," Croda Inc.; "AMINOL," Finetex, Inc.; and "T-TERGAMIDE," Harcros Chemicals, Inc. A preferred embodiment is cocoamide DEA, which surprisingly shows excellent pesticidal activity. Also, DEA fatty acids can be readily prepared by reacting DEA with a fatty acid or fatty acid-containing composition. The fatty acid composition may be, for example, a coconut fatty acid composition. DEA can be obtained from Ashland Chemical, Inc. The coconut fatty acid starting material can be obtained from Henkel Corporation. DEAs can be made using standard procedures as described, for example, in *Fatty Acids,* E. H. Pryde, ed., 1979, The American Oil Chemists' Society. Sources of fatty acids other than coconut oil can also be utilized. Examples of other fatty acid sources include soy, palmitic, stearic, and tallow fatty acids. Preferably, the source of fatty acids would comprise fatty acid compositions with about C9 to about C18 chain lengths. The following table provides an analysis of a typical coconut fatty acid composition.

TABLE 1

| Fatty Acid | Length | % |
| --- | --- | --- |
| Lauric | 12 | 48 |
| Myristic | 14 | 20 |
| Palmitic | 16 | 10 |
| Oleic | 18:1 | 10 |
| Capric | 10 | 5 |
| Caprylic | 8 | 4 |
| Linoleic | 18:2 | 1 |

Tank mixes of fatty acids can be prepared according to procedures which are well known to those skilled in the art. For example, a fatty acid spray oil can be prepared using a solvent solution or emulsion of the fatty acid, a surfactant, and sufficient water to dilute the mixture to the desired concentration. Salts of fatty acids are readily dispersable or soluble in water.

The surfactants which may be used to emulsify the fatty acid in the aqueous formulations can be any of the non-phytotoxic surfactants, which are customarily used in preparing formulations for use on agricultural crops. The composition of the subject invention may also be combined with a spray oil as described in U.S. Pat. No. 4,560,677.

Fatty acids which can be used according to the subject invention are widely available and are sold under a variety of tradenames including "M-PEDE," "SCYTHE," "SHARPSHOOTER," "DE MOSS," and "SAFER" Insecticide Concentrate (SIC). As used herein, the term "SHARP-SHOOTER" refers to an 80% "SHARPSHOOTER" formulation which consists of 80% pelargonic acid, 2% emulsifier (such as Dowfax 32B) and 18% surfactant (such as Stepfac 8170). Also, fatty acids are readily available as components of natural products. For example, commonly available compositions such as citrus seed extracts and coconut oil can be used to supply the fatty acid component for use according to the subject invention.

II. Control of Fungal or Bacterial Plant Pathogens

In the first of three major embodiments, the subject invention concerns the in situ use of fatty acids and their salts or derivatives for the control of fungal and bacterial plant diseases. This mode of action is very compatible with other chemical and biological control approaches and fits well into the alternative pest control strategy which society is demanding.

The compositions and methods described herein can be used to control a broad range of fungal and bacterial targets. These targets include, but are not limited to species of Penicillium (i.e., *expansum, digitatum, italicum*), Botrytis sp., Monilinia sp., Alternaria sp., Aspergillus sp., Rhizopus sp., members of the Erisyphales (powdery mildews Sphaerotheca sp., Erisyphe sp., Uncinula sp., Podosphaera sp.), members of the Peronosporales (downy mildews, Phytopthora sp., Pythium sp., Peronospora sp.) Hemibasidiomycetes (rusts and smuts), Venturia sp., Cercospora sp., Pseudocercosporella sp., Cercospora sp., Cercosporidium sp., Fusarium sp., Ophiostoma sp. and other wood staining fungi, and Diplodia sp., other targets include Erwinia sp., Pseudomonas sp., and Xanthomonas sp. These targets can be controlled on seeds, corms, bulbs, flowers, stems, leaves exposed roots and fruits of plants including but not limited to grapes, pears, apples, peaches, nectarines, grapefruit, cherries, apricots, lemons, oranges, mangos, bananas, tangerines, potatoes, tomatoes, cucumbers, lettuce, rice, wheat, rye and other cereals, flower crops, and almonds. As used herein, the term "produce" includes, but is not limited to, any of the plant surfaces listed above. Also, as used herein, the term citrus refers to fruits such as oranges, lemons, limes, grapefruit, and the like. The compositions can also be applied to surfaces such as freshly cut lumber for the control of fungal or bacterial targets. The fatty acid compositions of the subject invention can be used to control microbial plant disease on both dormant and non-dormant plant tissue. As known by those skilled in the art, non-dormant tissue includes growing vegetation and fruits (pre- and post-harvest). Control of microbial plant pathogens on non-dormant tissue without phytotoxicity is particularly surprising and advantageous.

In one specific example, it has been discovered that pelargonic acid and its salts or derivatives, in a concentration of about 0.25 to about 3% w/v, have excellent curative activity against established fungal infections of produce (Examples 2 through 5). If produce is wounded and infected with the pathogen and then 18–24 hours later it is treated, disease does not develop. Disease control is not observed if the fatty acids are applied at the same time the fungus is inoculated or prior to that inoculation. Similarly, applications of about 2% "M-PEDE" (mainly salts of c18 fatty acids) or about 0.5% pelargonic acid or about 0.75–1% potassium cocoate can dramatically reduce further sporulation when applied to plants which are already severely infected with powdery mildew pathogens. Again, application of the same fatty acids to the plants prior to infection (preventative) are ineffective.

Thus, the unexpected antifungal and antibacterial activity of fatty acids which we have now observed pertains specifically to their ability to eradicate existing infections. As is shown in Examples 2 through 5, fatty acids are capable of arresting disease development in Penicillium inoculated lemons. This is a wound pathogen, and by the time citrus fruit reaches the packing house, infections of harvesting wounds are typically well established (12–24 hours) and require therapeutic action.

The utility of fatty acids and their derivatives for therapeutic control is further documented in Examples 6 and 7 where pelargonic acid shows curative activity against *Botrytis cinerea* infection of pear, *Monilinia fructicola* infection of nectarine, and Penicillium infection of lemons and oranges.

In these cases where fatty acids are useful for eradication of existing infections of fruit, the further protection of that fruit from subsequent infections can be achieved by the simultaneous or subsequent application of a fungicide, bactericide, or a biological control organism in a dip or spray application. This application can also be made along with the application of various waxes or finishes which are commonly used with fruit. The formulation of such applications can also include nutrients which will benefit the establishment of the biocontrol organism.

Fatty acids are also active against obligate parasites such as powdery mildews. Attempts to control these diseases currently involve rigorous, preventive control programs based on either sulfur products or synthetic fungicides which inhibit ergosterol biosynthesis. If a mildew epidemic becomes too advanced, it is extremely difficult to use those same products to halt its further spread. As shown in Example 8 through 21, fatty acid compositions which lack the ability to prevent mildew infection are capable of killing severe, established infections. As such, they are highly advantageous as "rescue treatments" in the event of severe mildew infestations.

One element of this invention concerns the concentration range for the efficacious use of fatty acid compositions. At very low concentrations there is no activity, at an intermediate range there is desirable activity, but at higher concentrations the host plant can be damaged and this can actually enhance infection (e.g., in Example 3 where concentrations of pelargonic acid of about 0.5% and higher were more severely infected than the water control). In the case of powdery mildew control with pelargonic acid (Example 8), concentrations of about 1% and above can become highly phytotoxic as this fatty acid is used commercially as an herbicide. The safety margin between antimicrobial activity and phytotoxicity can be widened by the formulation of the fatty acid. In particular, certain salts are much less phytotoxic and only slightly less fungicidal than the parent acid (Example 4). Appropriate formulations and concentrations can be readily ascertained by those skilled in this art using the teachings of the subject invention.

A. Combination of fatty acids with other agents. The fatty acids of the subject invention do not show preventive activity; however, one aspect of the first embodiment of the subject invention is the combination of the potent, therapeutic activity of fatty acid compositions with the preventive action of chemical fungicides, bactericides, or the exclusionary and/or competitive capabilities of biological control agents. The benefits of these combinations fall into two main categories: fungicide and bactericide rate reductions, and enhanced activity against pathogens of interest.

The potent, curative activity of the fatty acid compositions of the subject invention combined with other fungicides or bactericides makes it possible to achieve the same level of control while using a smaller quantity of the non-fatty acid fungicide or bactericide component of the mixture. We have discovered that the compositions of the present invention can comprise a mixture of components wherein said mixture is sufficiently active so that application of the composition enables utilization of reduced amounts of each of the active ingredients while still providing effective activity. This is significant because lower use rates lead to lower residues on the crop or in the environment, lower costs of application, an expansion of the margin between crop safety and efficacy for fungicides which can be phytotoxic (thus enhancing their safety or expanding the crops, varieties or timings for their use), and lower total "market basket" exposure for a multi-use fungicide or bactericide.

We have discovered that combinations of other fungicides or bactericides with fatty acids offer additional advantages because of the particular mode of action of these materials. One such advantage is a reduction in selection pressure for resistant forms. It is often difficult to find appropriate resistance mixing partners for systemic/curative fungicides since materials which have a different mode of action and which are also curative are rare. Mixtures of curative and non-curative fungicides are considered to be less desirable for resistance management. Use rates of fungicides can also be lowered in cases where their current use rate is high to provide control partially tolerant pathogen strains.

Many fungicides or bactericides have excellent preventive efficacy, but are ineffective for the eradication of existing infections. Used alone, these compounds must be continually reapplied to maintain a constant, protective cover over the crop tissues. Combinations of such material with a curative, fatty acid product increases overall efficacy of the disease management strategy, allows less frequent use of the protectant, and extends to new crops or regions a control program which uses the fungicide or bactericide in question.

Chemical control agents which can be combined with fatty acids according to the subject invention include, but are not limited to benomyl, borax, captafol, captan, chlorothalonil, various formulations containing copper; various formulations containing zinc; dichlone, dicloran, iodine, various ergosterol biosynthesis inhibiting fungicides including but not limited to fenarimol, imazalil, myclobutanil, propiconazole, prochloraz, terbutrazole, flusilazole, triadimefon, and tebuconazole; folpet, iprodione, mancozeb, maneb, metalaxyl, oxycarboxin, oxytetracycline, PCNB, pentachlorophenol, quinomethionate, sodium arsenite, sodium DNOC, sodium hypochlorite, sodium phenylphenate, streptomycin, sulfur, thiabendazole, thiophanate-methyl, triforine, vinclozolin, zineb, ziram, tricyclazole, cymoxanil, blasticidin, validimycin. The fatty acids can also be combined with various spray oils.

Specifically exemplified herein is the combination of a fatty acid component with a sulfur compound. In a preferred embodiment, the fatty acid component is a potassium cocoate which is combined with sulfur. Alternatively, salts of about C9 to about C12 fatty acids can be used with sulfur. Surprisingly, this combination results in excellent fungicidal activity (preventative and curative) without phytotoxicity.

III. Use of Fatty Acid Compositions in Niche-Clearing Methods

The broad spectrum antimicrobial activity of fatty acids are particularly advantageous for a unique strategy which combines fatty acid compositions with various biocontrol agents. A common limitation of biological controls has been the inability of the desired live control agents to colonize treated surfaces. The existing microflora of that surface, if well developed, can preclude the establishment of the applied organism. The fatty acid compositions of the subject invention are useful for disrupting existing microflora (pathogens and saprophytes), making it more likely that a biocontrol organism will successfully colonize the surface if it is applied at the same time or soon after the fatty acid composition. This is a particularly attractive possibility with fatty acid compositions because they do not persist on the plant at effective concentrations. A further extension of this concept involves the addition of a nutrient or other enrichment agent to the fatty acid plus biological strategy. It is within the skill of a person trained in this art to use the teachings presented herein to devise the appropriate compositions of fatty acids, biologicals and enrichment agents.

The biological control agents that can be used according to the subject invention include but are not limited to Bacillus sp., Pseudomonas sp., Trichoderma sp., Erwinia sp., Pichia sp., Candida sp., Cryptococcus sp., Talaromyces sp., *P. fumosoreus, B. bassiana,* Chaetomium sp., Gliocladium sp., Aureobasidium sp., Dabaryomyces sp., Exophilia sp., Ampelomyces sp., and Mariannaea sp. One embodiment of the subject invention is to select for biological agents which are tolerant to and thus well suited to a use in combination with fatty acid compositions.

Spray oils (also known as agricultural spray oils) which can be used as negative selection agents according to the subject invention include, but are not limited to, paraffin oils such as 6N, 7N, 9N, and 11N sold by the Sun Oil Co. of Philadelphia, Pa. Other negative selection agents include, but are not limited to, carbonate salts, alcohols, inorganic metals and combinations of these various agents. Positive selection agents which can be used according to the subject invention include, but are not limited to, yeast ghosts, bacterial ghosts, algal ghosts, complex carbohydrates, simple carbohydrates, organic nitrogen, or combinations of these agents.

IV. Pesticidal Use of Fatty Acid Compositions

The subject invention further concerns the discovery of fatty acid derivatives with excellent pesticidal activity. As used herein, pests include, but are not limited to, insects and mites. Specifically, fatty acid amides have been found to have particularly advantageous pesticidal properties. Thus, compounds having the Formula IA can be used in pesticidal applications according to this embodiment of the invention. Specifically disclosed herein is the excellent pesticidal activity of diethanolamine amide derivatives of fatty acids. One preferred embodiment is cocoamide DEA, which can be prepared by reacting coconut fatty acid preparations with diethanolamine. As shown in Example 15, these compounds are highly effective in controlling pests.

Following are examples which illustrate procedures, including the best mode, for practicing the invention. These examples should not be construed as limiting. All percentages are by weight and all solvent mixture proportions are by volume unless otherwise noted.

EXAMPLE 1

Activity of Selected Fatty Acids Against Plant Pathogens

Various concentrations of pelargonic acid in one of two forms was added to molten potato dextrose agar (PDA) and poured into small disposable petri plates. The acid was added either as an emulsified free acid or as the potassium salt of the pure acid. Control plates were made by adding comparable concentrations of the surfactants in the pelargonic acid formulation or by adding water. To these plates were added suspensions of the spores of Penicillium digitatum or Botrytis cinerea. These plates were observed 3 days later for fungal germination and growth and the results are shown in Table 2.

TABLE 2

| Treatment | % a.i. | Penicillium digitatum | Botrytis cinerea |
|---|---|---|---|
| 80% formulation | 2.0 | − | − |
| (emulsified acid) | 0.5 | − | − |
|  | 0.125 | − | − |
|  | 0.03 | − | − |
| 80% formulation | 2.0 | + | + |
| surfactant blank | 0.5 | + | + |
| (equivalent dilutions) | 0.125 | + | + |
|  | 0.3 | + |  |
| Potassium salt of | 2.0 | − | − |
| pelargonic acid | 0.5 | − | − |
|  | 0.125 | − | − |
|  | 0.03 | + | − |
| Media control | − | + | + |

+ = germination
− = no germination

EXAMPLE 2

A Comparison of Preventive and Curative Activity of Pelargonic Acid for the Control of Green Mold Infections of Lemons Lemons grown without the application of synthetic chemicals were harvested and inoculated at 5 marked locations with spores of Penicillium digitatum ($10^7$ conidia/ml) by pricking to a depth of 2 mm with an 18-gauge needle dipped in a spore suspension. After inoculation the lemons were held in closed plastic boxes over wet paper towel at 22° C. The lemons were either not-dipped or dipped in a 1% a.i. pelargonic acid suspension at 0, 5, 16 or 24 hours after inoculation. Infection was rated 4 days after inoculation based on the number of wounds which became infected (Table 3).

TABLE 3

| Treatment | Application Timing (hours after inoculation) | Percent Infection 4 days after inoculation |
|---|---|---|
| None | — | 84 |
| 1% a.i. | 0 | 100 |
|  | 5 | 58 |
|  | 16 | 2 |
|  | 24 | 4 |

EXAMPLE 3

Dose Response Characteristics of Pelargonic Acid for the Control of Green Mold of Lemons Lemons grown without the application of synthetic chemicals were harvested and surface disinfected by washing in a 1:10 dilution of household bleach. They were inoculated at 5 marked locations with spores of Penicillium digitatum ($10^5$ conidia per ml) by pricking to a depth of 2 mm with an 18-gauge needle dipped into the spore suspension. They were incubated for 18 hours at 22° C. in closed, plastic boxes on trays above wet paper towels. At that time they were removed and immersed for 15 seconds in dilutions of pelargonic acid or in water. The lemons were allowed to drain-off and then returned to the boxes to incubate at 22° C. for 13 days. Disease was rated 13 days later based on the percentage of wound sites which became infected (Table 4).

TABLE 4

| Treatment | % a.i. | $10^5$ conidia/ml % infection 13 DAT |
|---|---|---|
| 80% formulation | 1.0 | 80 |
| (emulsified suspension | 0.5 | 50 |
| of pelargonic acid) | 0.25 | 0 |
|  | 0.125 | 0 |
|  | 0.063 | 0 |
| Water control | — | 30 |

EXAMPLE 4

Efficacy of Pelargonic Acid in Various Forms for the Control of Green Mold of Lemons Lemons grown without the application of synthetic chemicals were harvested and surface disinfected by washing in a 1:10 dilution of household bleach. They were inoculated at 5 marked locations with spores of Penicillium digitatum ($10^6$ conidia per ml) by pricking to a depth of 2 mm with an 18-gauge needle dipped into the spore suspension. They were incubated for 18 hours at 22° C. in closed, plastic boxes on trays above wet paper towels. At that time they were removed and immersed for 15 seconds in dilutions of an emulsified suspension of pelargonic acid in a surfactant blank without the fatty acid, or in pelargonic acid which was converted to the potassium salt by titration to pH 7 with 10 N KOH. The lemons were allowed to drain-off and then returned to the boxes to incubate at 22° C. As in the other examples, the spore concentrations and the incubation temperature used constitutes a severe test of the ability of an agent to provide control of this disease. Either a delay in disease onset or in the highest disease level realized constitutes an indication of useful control under actual storage conditions. Disease was rated 5 days later based on the percentage of wound sites which became infected (Table 5).

TABLE 5

| Treatment | % a.i. | % infection 5 days after inoculation |
|---|---|---|
| Pelargonic acid | 2.0 | 8 |
|  | 0.5 | 12 |
|  | 0.125 | 10 |
| Pelargonic acid | 2.0 | 0 |
| converted to | 0.5 | 8 |
| potassium salt | 0.125 | 18 |
| Surfactant blank | 2.0 | 70 |
|  | 0.5 | 64 |
|  | 0.125 | 90 |

EXAMPLE 5

The Activity of Various Salts and Esters of Pelargonic Acid for the Control of Lemon Green Mold Lemons were surface disinfected in 10% bleach and dried. These were stab-inoculated with a 3 mm long, 18-gauge needle dipped into a spore suspension containing $10^6$ spores/ml of Penicillium digitatum. Five injuries were made in each fruit along a diagonal mark. The lemons were incubated at 22° C. for 18 hours at high humidity. The fruit was then treated with various salts or esters of pelargonic acid.

To synthesize ethylene glycol monopelargonate, 51.5 g pelargonic acid and 51 g ethylene glycol were dissolved in 200 ml of dichloromethane, and 20 drops of $H_2SO_4$ were added to the mixture. This mixture was stored at room temperature for 6 days. After 6 days, 150 ml of 0.1 N NaOH was added to the reaction mixture which was then vigorously shaken. The dichloromethane layer (lower layer) was collected and washed with saturated NaCl solution.

After drying on $Na_2SO_4$, the chloroform layer was evaporated. Remaining oil (38 g) was subjected to vacuum distillation yielding 34.8 g (yield 53.8%) of ethylene glycol monopelargonate (b.p. 135–137° C. (7 mm Hg)).

A ready-to use aqueous formulation of the isopropylamine salt of pelargonic (nonanoic) acid was prepared. The pelargonic acid was obtained as "EMERY 1202" from Quantum Chemical Corporation, Cincinnati, Ohio, and is a mixture of normal fatty acids of chain length 8, 9, and 10, with C9 being predominant. Various aqueous formulations were prepared with up to 20% active ingredient as the fatty acid and up to 6% isopropylamine, with the balance being water. The requisite amount of pelargonic acid was dispensed into an appropriate mixing vessel and the mixing initiated. The requisite amount of water was added to the acid and the acid dispersed into the water by mixing, thus forming a cloudy, unstable dispersion. Isopropylamine (Aldrich Chemical Company, Milwaukee, Wis.) was added slowly, with continuous mixing, in sufficient quantity to bring the pH of the formulation to approximately 7.4–7.8. At this approximate pH the cloudy dispersion became translucent as the fatty acid isopropylamine salt became water soluble.

The 2% treatments were applied with a cotton swab, the lower concentrations were applied by dipping the fruit in the test solution. The fruit was incubated in the same conditions for an additional 72 hours, after which the infection was rated based on the number of injury sites exhibiting characteristic softening and sporulation. The percent disease control was calculated by comparing the level of infection to that in the untreated check (83% of injuries infected).

TABLE 6

| Treatment | concentration applied | percent disease control |
| --- | --- | --- |
| Potassium salt | 2.0 | 83 |
| | 0.5 | 90 |
| | 0.125 | 86 |
| Isopropyl amine salt | 2.0 | 71 |
| | 0.5 | 95 |
| | 0.125 | 81 |
| Mono-ethylene glycol ester | 2.0 | 56 |
| | 0.5 | 76 |
| | 0.125 | 54 |
| Ethyl ester | 2.0 | 16 |
| | 0.5 | 16 |
| | 0.125 | 0 |
| Pelargonic acid emulsion | 2.0 | 69 |
| Ammonium salt | 2.0 | 98 |

EXAMPLE 6

Treatment of Citrus with Fatty Acid Compositions

All fruits were washed with 1 00 ppm chlorine followed by a fresh water rinse. The pathogens (*Penicillium digitatum* or *Penicillium italicum*) were inoculated by painting a scratch injury (20–30 mm long by 1.5–2 mm deep) with a cotton swab dipped into a spore suspension of $1^6$ conidia/ml. 20–24 hours after inoculation, fruit was treated by dipping or, in some cases, using a commercial style washer/waxer machine. The fruit was then stored at 70° F. at 80–90% RH for 7 days or when the check treatment had become 100% infected. For each treatment there were three replicates of 15–20 fruits. Percent decay was calculated by the ratio of diseased to sound fruit regardless of the severity of the disease lesion. Table 7 shows the results on lemons. The treatments were applied in packout wax. Table 8 shows the results on oranges with dip treatment. Table 9 shows the results on lemons dipped for 3 minutes at 105° F., then rinsed. Table 10 shows results on lemons dipped and then treated in the storage wax. Table 11 shows dip treatment of early and late Valencia oranges.

TABLE 7

| | Rate (ppm active) | Percent Decay |
| --- | --- | --- |
| wax only | — | 55 |
| Potassium pelargonate | 0.5% | 63 |
| | 0.75% | 40 |
| | 1.0% | 21 |
| Thiabendazole | 5000 ppm | 8 |

TABLE 8

| Treatment | Concentration | Fruit Injury | Percent Decay |
| --- | --- | --- | --- |
| Check | — | no | 100 |
| SOPP | 5000 ppm | no | 18 |
| Potassium pelargonate | 0.5% | no | 42 |
| | 1.0% | no | 25 |
| | 1.5% | no | 25 |
| | 2.0% | no | 22 |
| | 2.5% | no | 22 |
| Pelargonic acid | 0.5% | no | 63 |
| | 1.0% | yes | 40 |
| | 1.5% | yes | 40 |
| | 2.0% | yes | 20 |
| | 2.5% | yes | 22 |

TABLE 9

| Treatment | Concentration | Percent Decay |
| --- | --- | --- |
| Check | — | 100 |
| Potassium pelargonate | 1.0% | 90 |
| | 2.0% | 15 |
| Soda Ash | 3.0% | 21 |

TABLE 10

| Dip Treatment | Wax Treatment | Percent Decay at 7 Days | Percent Decay at 22 Days |
| --- | --- | --- | --- |
| Check | Check | 100 | 100 |
| 3% Soda Ash | 2000 ppm Imazilil | 0 | 9 |
| 5% Borax | 2000 ppm Imazilil | 0 | 0 |
| 2% Potassium pelargonate | 2000 ppm Imazilil | 0 | 22 |
| 2% Potassium pelargonate | 0.5% Potassium pelargonate | 12 | 42 |
| 2% Potassium pelargonate | 1.0% Potassium pelargonate | 3 | 25 |

TABLE 11

| Treatment | Percent Decay Late Valencia | Percent Decay Early Valencia |
| --- | --- | --- |
| Check | 100 | 100 |
| 1% Potassium pelargonate, rinsed | 40 | 8 |

TABLE 11-continued

| Treatment | Percent Decay Late Valencia | Percent Decay Early Valencia |
|---|---|---|
| 2% Potassium pelargonate, rinsed | 22 | 4 |
| 1% Potassium pelargonate, not rinsed | 30 | 0 |
| 2% Potassium pelargonate, not rinsed | 2 | 0 |
| 0.5% SOPP, rinsed | 0 | 0 |

EXAMPLE 7

Efficacy of Pelargonic Acid and its Salt for the Control of *Botrytis cinerea* Infection of Pears and of *Monilinia fructicola* Infection of Nectarines Undamaged apples were prick inoculated with spores of Botrytis cinerea (106 conidia/ml) by dipping an 18 gauge needle in the spore suspension and using it to make a 2 mm deep wound at 5 locations on each of 4 fruits. Nectarines were similarly inoculated with Monilinia fructicola ($10^6$ cfu/ml). The fruits were then placed in closed, plastic boxes on trays above wet paper towels. After 18 hours of incubation at 22° C., the fruits were removed and dipped for 15 seconds in water, in dilutions of an emulsified suspension of pelargonic acid or in pelargonic acid converted to its potassium salt by titration to pH 7 with 10 N KOH. They were returned to the boxes and allowed to incubate for 7 or 14 days at 22° C. at which time they were rated for percent infection based on the number of wounds which developed decay typical of the disease in question (Table 12).

TABLE 12

| Treatment | % a.i. | % Infection Botrytis Pears 7 DAT | % Infection Monilinia Nectarines 7 DAT | % Infection Monilinia Nectarines 14 DAT |
|---|---|---|---|---|
| Emulsified acid | 1.0 | 35 | 0 | 33 |
|  | 0.25 | 35 | 0 | 33 |
|  | 0.063 | 70 | 45 | 100 |
| Pelargonic acid converted to potassium salt | 1.0 | 15 | 0 | 25 |
|  | 0.25 | 20 | 25 | 80 |
|  | 0.063 | 30 | 70 | 100 |
| Water control | — | 55 | 50 | 85 |

EXAMPLE 8

Dose-Response Effects of Various Fatty Acids for the Control of Powdery Mildew on Kentucky Bluegrass Kentucky Bluegrass plants were grown in 6-cell Jiffy strips for four weeks, cut to 5 cm and transplanted cell-by-cell into a 4inch plastic pot with Promix putting medium. One half of the pots were allowed to become naturally infested with powdery mildew (*Erysiphe graminis*) so that 85–100 percent of the leaf area was covered with sporulating colonies of the fungus. The other half of the pots were grown without exposure to powdery mildew. Both types of plants were treated with water (as a control), with dilutions of "M-PEDE" (mainly potassium salts of c18:0 fatty acids), or with dilutions of emulsified pelargonic acid. The already infected plants thus received a "curative" treatment. One day after the treatment, the as-yet uninfected plants ("preventive treatment") were inoculated by shaking heavily infected plants over the pots. All plants were then incubated in a greenhouse and at different intervals were evaluated for percent coverage of the leaf surface by powdery mildew. These results are expressed as percent control relative to the water check for the curative treatments and percent infection for the preventive treatments (Table 13).

TABLE 13

| Treatment | % a.i. | Curative % Control 15 DAT |
|---|---|---|
| "M-PEDE" (potassium salts of principally c18 fatty acids) | 1.0 | 90 |
|  | 0.5 | 80 |
|  | .25 | 57 |
|  | .125 | 20 |
| Emulsified pelargonic acid | 0.8 | 97 |
|  | 0.4 | 82 |
|  | 0.2 | 73 |
|  | 0.1 | 43 |
| Water control | — | 0 |

EXAMPLE 9

Control of Mildew on Roses

Roses (cv 'Samantha') in a commercial greenhouse were treated five times on a weekly basis for control of powdery mildew. Applications were made with a backpack sprayer at 100 gpa. No plant or flower injury occurred in any of these treatments. Because this was a commercial greenhouse, it was not possible to leave an untreated check. Under these conditions, untreated roses would have extremely severe mildew infection. What this data shows is that the fatty acids can be applied many times without injury and that the mildew is kept under control, decreasing over time. The results are shown in Table 14.

TABLE 14

| Treatment | Concentration (percent active) | Mildew colonies per plot after 3 weeks of treatment | Mildew colonies per plot after 4 weeks of treatment |
|---|---|---|---|
| M-PEDE (Potassium oleate) | 0.75 | 162 | 30 |
|  | 0.5 | 162 | 81 |
| Potassium cocoate | 0.6 | 73 | 16 |
|  | 0.4 | 55 | 36 |

EXAMPLE 10

Control of Powdery Mildew with Fatty Acids and Various Derivatives

Wheat var. Newton was grown for one week in a 17° C. growth chamber. After one week wheat powdery mildew (*Erysiphe graminis*) was applied to seedlings by shaking infected plants over the top. After 5 days treatments were applied with an airbrush. Materials were applied to wet the leaves but without excessive runoff. This approximated 200 to 300 gallons per acre. Infected plants were placed in screen cages in a 17° C. growth chamber. There were 6 replicate pots per treatment with three plants in each pot. Plants were rated for visible mildew colonies 5–7 days after inoculation. The top ⅓ of the first true leaf was rated for percent coverage with mildew. Results shown in Table 15 are expressed as percentage control as compared to either water or no treatment.

TABLE 15

| Compound | Rate (ai) | % Control |
| --- | --- | --- |
| "M-PEDE" | 0.8 | 87 |
| "M-PEDE" | 0.4 | 58 |
| "M-PEDE" | 0.2 | 12 |
| Soyamide DEA | 0.2 | 76 |
| Soyamide DEA | 0.1 | 58 |
| Potassium Cocoate | 0.6 | 90 |
| Potassium Cocoate | 0.3 | 90 |
| Potassium Cocoate | 0.15 | 56 |
| Cocoamide DEA | 0.1 | 82 |
| Cocoamide DEA | 0.05 | 76 |

EXAMPLE 11

Ripe lemons were marked with a line using a felt-tip pen. Five three-millimeter deep stab injuries were made along the line using an 18-gauge stainless steel needle. A cotton swab was used to apply a spore suspension of *Penicillium italicum* to those injuries ($3 \times 10^6$ spores/ml). The lemons were then incubated for 24 hours at 22° C. in a closed container. After this incubation, lemons were immersed in various test solutions for a few seconds and then returned to a closed, humid box for 22° C. incubation for 10 days. At the end of that time, the lemons were rated for "blue mold" decay with the following results:

TABLE 16

| Test Solution | Percent "Blue Mold"-Damaged Lemons |
| --- | --- |
| Water | 69 |
| Pelargonic acid -- 0.15% a.i., oil/water emulsion | 35 |
| Cocoamide DEA -- 0.4% in water | 50 |

Because the lemons used in this test were ripe and because the inoculum rate was high, even the incomplete control observed with the chemical treatments was significant.

EXAMPLE 12

Control of Mildew on Grape Plants

In this grape test, both potassium cocoate and potassium oleate were tested at low concentrations mixed with sulfur. The safety with the cocoate is excellent.

Applications of the sulfur and fatty acid composition mixtures were made to a commercial vineyard (cv. 'Chardonnay') using a "mist blower" sprayer applying 100 gallons of spray per acre. The expanding leaves were rated 4 days later for any damage from the earlier spray. The form of sulfur used in this experiment is the product "Thiolux," which is a wettable 80% sulfur formulation. Results are shown in Table 17.

TABLE 17

| Treatment | Concentration(s) (% active ingredient) | Observations of expanding leaves |
| --- | --- | --- |
| Potassium cocoate | 0.3% | no injury |
|  | 0.5% | no injury |
| Potassium cocoate plus | 0.3%, 0.48% | no injury |
| Thiolux | 0.5%, 0.48% | no injury |
| Potassium oleate | 0.75% | no injury |
| Potassium oleate plus | 0.75%, 0.48% | many expanding leaves |

TABLE 17-continued

| Treatment | Concentration(s) (% active ingredient) | Observations of expanding leaves |
| --- | --- | --- |
| Thiolux |  | severely burned |
| Thiolux | 0.48% | no injury |

EXAMPLE 13

Evaluation of Phytotoxicity of Fatty Acid Component Combined with Sulfur

An experiment was conducted on 2-year old grape vines growing outdoors in 3-gallon containers. The vines had new shoot growth of 3 to 12 inches and were growing rapidly. Test materials were applied to these using a syringe hand sprayer which makes a spray through a normal agricultural flat fan nozzle. The application was "high volume," consisting of 40 ml per pot-an amount which led to runoff from the treated leaves. Following the application the vines were moved inside overnight to a lighted growth chamber with 28° C. daytime temperature and 25° C. nighttime temperature. After spending approximately 16 hours in this chamber, the plants were removed for phytotoxicity evaluation expressed as % leaf damage on expanding leaves. The test materials included various fatty acids, fatty acid derivatives, wettable sulfur ("THIOLUX"), and mixtures of the former materials with sulfur. Each material was tested at the desired, fungicidal use rate for the field. The results are presented in Table 18.

TABLE 18

Phytotoxicity ratings of grape shoots

| Test material | Concentration % a.i. | % leaf injury on expanding leaves |
| --- | --- | --- |
| "M-PEDE" (potassium oleate) | 0.75 v/v | none |
| "M-PEDE" plus sulfur | 0.75 v/v<br>0.48 v/v | 80–90% |
| Potassium cocoate | 0.4 v/v | none |
| Potassium cocoate plus sulfur | 0.4 v/v<br>0.48 w/v | 10–20% |
| Potassium cocoate | 0.375 v/v | none |
| Potassium cocoate plus sulfur | 0.375 v/v<br>0.48 w/v | 0–5% |
| Cocoamide-DEA | 0.25 w/v | none |
| Cocoamide-DEA plus sulfur | 0.25 w/v<br>0.48 w/v | 70–80% |
| Cocoamide-DEA | 0.15 w/v | none |
| Cocoamide-DEA plus sulfur | 0.15 w/v<br>0.48 w/v | 40–50% |

EXAMPLE 14

The Use of Various Agents Including Fatty Acids for the Disruption of Peanut Leaf Surface Microflora Peanut plants were grown in the greenhouse for three weeks, after which time they were sprayed with a leaf-washing suspension from local landscape plants. This provided a charge of potential leaf surface-colonizing microbes. These plants were then held each night in a 22° C. dew chamber and placed outdoors in full sun each day. This step provides realistic selection pressure for normal leaf surface microflora. After three days in this regime, the plants were treated each day with various agents with the potential to exercise selective pressure on the population of microbes and thus to enrich for organisms tolerant to or favored by the applied agent. The agents consisted of various combinations of potassium carbonate (0.05%), the potassium salt of pelargonic acid (0.5%), and yeast ghosts ($10^8$ cells/ml, Baker's yeast killed by boiling and washed extensively by centrifugation). The potassium carbonate and pelargonic acid were considered "negative" selection agents and the yeast ghosts were considered a "positive" selection agent. These agents were applied on each of three days, during which time the plants continued to cycle between the dew chamber and sun exposure. At the end of this treatment period, individual leaves were harvested and washed to recover surface colonizing organisms. These washings were dilution-plated on both nutrient agar and potato dextrose agar, and the mean populations recovered are listed in Table 19.

TABLE 19

Mean colony forming units recovered per peanut leaf following enrichment with various agents

| Selection treatment applied | cfu/leaf on nutrient agar | cfu/leaf on potato dextrose agar |
| --- | --- | --- |
| 1. water | $1.9 \times 10^5$ | $4.4 \times 10^5$ |
| 2. yeast ghosts | $1.9 \times 10^6$ | $8.3 \times 10^5$ |
| 3. 0.5% K⁺ salt of pelargonic acid plus 0.05% potassium carbonate | $2.9 \times 10^4$ | $1.1 \times 10^4$ |
| 4. a combination of the components of treatments 2 and 3 above | $3.2 \times 10^4$ | $3.3 \times 10^4$ |

In addition to effects on the total surface populations recovered, these treatments also had evident effects on the composition of the microflora (based on colony size, morphology, color, and growth on different media). Following this enrichment procedure, individual colonies can be isolated. Microorganisms thus isolated can then serve as hosts for heterologous genes which may be transformed into said host. Advantageously, these heterologous genes could code for a protein which is toxic to a plant pest. Such toxins are widely known in the art as are the genes which code for these toxins. For example, it is well known that many *Bacillus thuringiensis* express proteins which are toxic to plant pests. B.t.s may be applied to plants, according to the subject invention, in conjunction with fatty acid treatment or, alternatively, B.t. genes coding for toxins may be placed into, and expressed in, other hosts which are particularly adapted to growth and persistence on plants, especially in the presence of fatty acids. Methods for inserting these genes into an appropriate host are also well known. See, for example, published European Patent Application 0 200 344. The transformed microorganism can then be applied to appropriate plants in need of protection from pests. The plants may first be treated with a fatty acid composition to clear away competing microbes and to control bacterial and fungal infection, if necessary. Once transformed microbes are applied to the plants, fatty acids may subsequently be applied to clear away competing or undesirable microbes. Applications of fatty acid may be accompanied by enrichment agents to assist the colonization of the desired microbes. Also, the desired microbes may be further transformed with additional gene(s) which make these microbes particularly adapted to selective enrichment.

EXAMPLE 15

Application of Microfloral Disruption Agents in a Field Enrichment Protocol

Agents with the potential to disrupt leaf and flower surface microflora were applied on 4 days during a 1 week period to tomato plants in a commercial production field. After this period, leaf washings from 15–20 separate leaflets or flowers were dilution-plated for each treatment and the number of colonies (yeasts and bacteria) were determined as reported in Table 20.

TABLE 20

Mean colony forming units recovered per leaflet or flower following a field selection protocol.

| Selection treatment | Recovery on Nutrient Agar | | Recovery on Potato Dextrose Agar | |
| --- | --- | --- | --- | --- |
| | Flowers | Leaves | Flowers | Leaves |
| 1. water | 16,250 | 5,200 | 1,175 | 1,488 |
| 2. yeast ghosts | 48,300 | 12,940 | 51,700 | 10,740 |
| 3. K⁺ salt of pelargonic acid | 8,375 | 6,141 | 1,225 | 741 |
| 4. 2 and 3 | 7,325 | 2,520 | 2,160 | 1,158 |

As in Example 12, these agents were able to alter both the density and composition of the microflora on leaves and flowers. As described in Example 12, microbes isolated after application of selection treatments can be used as excellent plant colonizers for application of recombinant toxin-producing microbes.

EXAMPLE 16

Insecticidal Activity of Fatty Acids and Various Derivatives

A colony of green peach aphids was maintained on lettuce at 17° C. in the growth chamber. For testing purposes, 10–20 aphids were transferred to detached lettuce leaves, which were placed in petri plates containing a moistened filter paper. Test solutions were applied at a rate of 1.5 ml per plate (200–300 gallons per acre). The covers were placed on the petri plates. The number of dead aphids was counted after 1 hour. Experience has shown that material efficacy under this test system is 8–10 time greater than real world conditions. For example, the effective insecticidal rates of "M-PEDE" in the field is 0.75–1.0% ai, whereas in this described test system, the lowest effective concentration is 0.13%. This relationship holds for other insecticidally active materials. Results are shown in Table 21. The compounds of the subject invention can be used as pesticides at concentrations from about 0.05% to about 1% or more.

TABLE 21

| Compound | Rate (ai) | % Control |
| --- | --- | --- |
| "M-PEDE" | 0.5 | 91 |
| "M-PEDE" | 0.25 | 87 |
| "M-PEDE" | 0.13 | 73 |
| "M-PEDE" | 0.06 | 45 |
| "M-PEDE" | 0.03 | 25 |
| Cocoamide DEA | 0.05 | 100 |
| Cocoamide DEA | 0.03 | 88 |
| Cocoamide DEA | 0.01 | 73 |
| Potassium Cocoate | 0.2 | 15 |
| Potassium Cocoate | 0.1 | 4 |

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for the control of established fungal or bacterial plant disease, wherein said method comprises applying a fungicidal or bactericidal amount of a diethanolamine derivative of a fatty acid to the situs of said plant disease, wherein said diethanolamine derivative of said fatty acid conforms to the following formula:

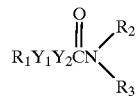

wherein
$R_1$=C5 to C19 saturated or unsaturated hydrocarbon
$Y_1$=H, $C_1$–$C_5$ hydrocarbon, or hydroxyl at any position along $R_1$
$Y_2$=H, $C_1$–$C_5$ hydrocarbon, or hydroxyl at any position along $R_1$
$R_2$=$CH_2CH_2OH$
$R_3$=$CH_2CH_2OH$.

2. The method, according to claim 1, wherein said method comprises applying a mixture of said diethanolamine derivatives of fatty acids wherein said fatty acids are selected from the group consisting of lauric acid, myristic acid, palmitic acid, oleic acid, capric acid, carpylic acid, and linoleic acid.

3. The method, according to claim 2, wherein said fatty acids are contained in a natural product which is formulated for the purpose of application to crops, produce, or wood products.

4. The method, according to claim 3, wherein said fatty acids are contained in coconut oil.

5. The method, according to claim 4, wherein said method comprises applying cocoamide DEA.

6. The method, according to claim 1, which further comprises the application of a synthetic or inorganic fungicide or bactericide.

7. The method, according to claim 6, wherein said synthetic or inorganic fungicide or bactericide is selected from the group consisting of benomyl, borax, captafol, captan, chlorothalonil, copper, zinc, dichlone, dicloran, iodine, fenarimol, imazalil, myclobutanil, propiconazole, prochloraz, flusilazole, triadimefon, tebuconazole, folpet, iprodione, mancozeb, maneb, metalaxyl, oxycarboxin, oxytetracycline, PCNB, pentachlorophenol, quinomethionate, sodium arsenite; sodium DNOC, sodium hypochlorite, sodium phenylphenate, streptomycin, sulfur, thiabendazole, thiophanatemethyl, triforine, vinclozolin, zineb, ziram, tricyclazole, cymoxanil, blasticidin and validamycin.

8. The method, according to claim 1, wherein said plant disease is caused by a pathogen selected from the group consisting of Penicillium sp., Botrytis sp., Monilinia sp., Alternaria sp., Aspergillus sp., Mucor sp., Rhizopus sp., Geotrichum sp., Diplodia sp., Colletotrichum sp., members of the orders Erisyphales, Peronosporales, Hemiascomycetes, Venturia sp., Cercospora sp., Cercosporidium sp., Pseudocercosporella sp., Myrothecium sp., Fusarium sp., Ophiostoma sp., Erwinia sp., Pseudomonas sp., and Xanthomonas sp.

9. The method, according to claim 8, wherein said pathogen is selected from the group consisting of Penicillium sp., *Botrytis cinera, Monilinia fructicola,* and powdery mildew fungi in the order Erisyphales.

10. The method, according to claim 1, wherein said fungal plant disease is affecting produce selected from the group consisting of citrus, bananas, mangos, tomatoes, pears, grapes, apples, peaches, cherries, apricots, and nectarines.

11. The method, according to claim 1, wherein said fatty acid is applied to foliage or produce before harvest.

12. The method, according to claim 1, wherein said fatty acid is applied to foliage or produce after harvest.

13. The method, according to claim 1, which further comprises the administration of a biocontrol agent.

* * * * *

UNITED STATES PATENT AND TRADEMARK OFFICE
CERTIFICATE OF CORRECTION

PATENT NO. : 6,103,768
DATED : August 15, 2000
INVENTOR(S) : Steven D. Savage, Steven L. Evans, Robert A. Haygood, Paul S. Zorner, Keith Jones It is certified that error appears in the above-indentified patent and that said Letters Patent is hereby corrected as shown below:

Column 13, Table 2, 4$^{th}$ Col., 8$^{th}$ line after heading: should have --+--.

Column 15, line 59: "1  00 ppm" should read --100 ppm--.

Column 17, line 20: "(106" should read --($10^6$--.

Column 17, line 56: "4inch" should read --4 inch--.

Column 22, line 17: "8,375" should read --8,275--.

Signed and Sealed this

Twenty-fourth Day of April, 2001

Attest:

NICHOLAS P. GODICI

Attesting Officer

Acting Director of the United States Patent and Trademark Office